US00PP30321P3

(12) United States Plant Patent
Holtmaat

(10) Patent No.: US PP30,321 P3
(45) Date of Patent: Mar. 26, 2019

(54) ***ECHINACEA* PLANT NAMED 'SUNNY292'**

(50) Latin Name: *Echinacea hybrida*
Varietal Denomination: Sunny292

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 0 days.

(21) Appl. No.: 15/731,580

(22) Filed: Jul. 3, 2017

(65) Prior Publication Data

US 2019/0008084 P1 Jan. 3, 2019

(51) Int. Cl.
*A01H 5/02* (2018.01)

(52) U.S. Cl.
USPC ..... Plt./428

(58) Field of Classification Search
CPC . A01H 5/025; A01H 5/02; A01H 6/14; A01H 6/1448; A01H 5/00
See application file for complete search history.

(56) References Cited

U.S. PATENT DOCUMENTS

PP24,631 P2 * 7/2014 Blom ..... A01H 5/00 Plt./428

OTHER PUBLICATIONS

Plants Nouveau 2016 Catalog Supplement (May 10, 2017) retrieved on May 21, 2018, retrieved from the Internet at https://issuu.com/angelatreadwell-palmer/docs/magazine0616, pp. 1-2, 7. (Year: 2017).*

* cited by examiner

*Primary Examiner* — June Hwu
(74) *Attorney, Agent, or Firm* — C. A. Whealy

(57) ABSTRACT

A new and distinct cultivar of *Echinacea* plant named 'Sunny292', characterized by its broadly upright plant habit; moderately vigorous growth habit; freely branching habit; strong flowering stems; numerous large single-type inflorescences with yellow orange-colored ray florets and dark yellow-colored receptacle spines; and good garden performance.

2 Drawing Sheets

Botanical designation: *Echinacea hybrida*.
Cultivar denomination: 'SUNNY292'.

BACKGROUND OF THE INVENTION

The present invention relates to a new and distinct cultivar of *Echinacea* plant, botanically known as *Echinacea hybrida*, and hereinafter referred to by the name 'Sunny292'.

The new *Echinacea* plant is a product of a planned breeding program conducted by the Inventor in Zuidwolde, The Netherlands. The objective of the breeding program is to develop new freely branching and relatively compact *Echinacea* plants with unique and attractive ray floret coloration.

The new *Echinacea* plant originated from an open-pollination in July, 2014 in Zuidwolde, The Netherlands of *Echinacea hybrida* 'Julia', disclosed in U.S. Plant Pat. No. 24,629, as the female, or seed, parent with an unknown selection of *Echinacea hybrida* as the male, or pollen, parent. The new *Echinacea* plant was discovered and selected by the Inventor as a single flowering plant from within the progeny of the stated open-pollination grown in a controlled greenhouse environment in Zuidwolde, The Netherlands in July, 2015.

Asexual reproduction of the new *Echinacea* plant by in vitro meristem culture in a controlled environment in Zuidwolde, The Netherlands since June, 2016 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunny292'. These characteristics in combination distinguish 'Sunny292' as a new and distinct *Echinacea* plant:

1. Broadly upright plant habit.
2. Moderately vigorous growth habit.
3. Freely branching habit.
4. Strong flowering stems.
5. Numerous large single-type inflorescences with yellow orange-colored ray florets and dark yellow-colored receptacle spines.
6. Good garden performance.

Plants of the new *Echinacea* can be compared to plants of the female parent, 'Julia'. Plants of the new *Echinacea* differ primarily from plants of 'Julia' in the following characteristics:

1. Plants of the new *Echinacea* are taller than plants of 'Julia'.

2. Plants of the new *Echinacea* are not as freely branching as plants of 'Julia'.
3. Plants of the new *Echinacea* flower later than plants of 'Julia'.

Plants of the new *Echinacea* can be compared to plants of *Echinacea hybrida* 'Cleopatra', disclosed in U.S. Plant Pat. No. 24,631. In side-by-side comparisons, plants of the new *Echinacea* differ primarily from plants of 'Cleopatra' in the following characteristics:

1. Flowering stems of plants of the new *Echinacea* are stronger than flowering stems of plants of 'Cleopatra'.
2. Plants of the new *Echinacea* are not as freely branching as plants of 'Cleopatra'.
3. Leaves of plants of the new *Echinacea* are darker in color than leaves of plants of 'Cleopatra'.
4. Ray florets of plants of the new *Echinacea* are more intense in color than ray florets of plants of 'Cleopatra'.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet is a side perspective view of a typical flowering plant of 'Sunny292' grown in a ground bed in an outdoor nursery and placed in a container for the photograph.

The photographs on the second sheet are close-up views of a typical inflorescence (upper photograph) and the upper surface of a typical leaf (lower photograph) of 'Sunny292'.

DETAILED BOTANICAL DESCRIPTION

The aforementioned photographs and following observations and measurements describe plants grown during the summer in ground beds in an outdoor nursery in Zuidwolde, The Netherlands and under cultural practices typically used in commercial *Echinacea* production. During the production of the plants, day temperatures ranged from 18° C. to 30° C. and night temperatures ranged from 6° C. to 18° C. Plants were six months old when the photographs and description were taken. In the following description, color references are made to The Royal Horticultural Society Colour Chart, 2015 Edition, except where general terms of ordinary dictionary significance are used.

Botanical classification: *Echinacea hybrida* 'Sunny292'.

Parentage:

*Female parent*.—*Echinacea hybrida* 'Julia', disclosed in U.S. Plant Pat. No. 24,629.

*Male parent*.—Unknown selection of *Echinacea hybrida*, not patented.

Propagation:

*Type*.—By in vitro meristem culture.

*Time to initiate roots, summer*.—About one week at temperatures about 25° C.

*Time to produce a rooted young plant, summer*.—About five weeks at temperatures about 21° C.

*Root description*.—Fine, fibrous; typically pale cream in color, actual color of the roots is dependent on substrate composition, water quality, fertilizer type and formulation, substrate temperature and physiological age of roots.

*Rooting habit*.—Freely branching; dense.

Plant description:

*Plant form and growth habit*.—Herbaceous perennial; broadly upright plant habit, narrow inverted triangle; freely branching habit with about seven lateral branches developing per primary branch; moderately vigorous growth habit; moderate growth rate.

*Plant height, soil level to top of foliar plane*.—About 52 cm.

*Plant height, soil level to top of floral plane*.—About 63.2 cm.

*Plant diameter or spread*.—About 51.9 cm.

*Lateral branches*.—Length: About 22.9 cm. Diameter: About 4 mm. Internode length: About 4.9 cm. Aspect: About 20° from vertical. Strength: Moderately strong. Texture and luster: Sparsely pubescent; moderately glossy. Color: Close to 144B.

Leaf description:

*Basal leaves*.—Arrangement: Alternate, simple. Length: About 18 cm. Width: About 6 cm. Shape: Narrowly ovate. Apex: Narrowly acute. Base: Attenuate. Margin: Entire, occasionally shallowly dentate. Texture and luster, upper and lower surfaces: Moderately pubescent, strigose, rough, slightly rugose; slightly glossy. Venation pattern: Pinnate. Color: Developing leaves, upper surface: Close to 144A. Developing leaves, lower surface: Close to 146B. Fully expanded leaves, upper surface: Darker than between NN137A and 147A; venation, close to 144B. Fully expanded leaves, lower surface: Close to 137B; venation, close to 144B. Petioles, basal leaves: Length: About 10.4 cm. Width: About 3 mm. Height: About 3 mm. Strength: Strong, flexible. Texture and luster, upper and lower surfaces: Sparsely pubescent; glossy. Color, upper and lower surfaces: Close to 144B.

*Cauline leaves*.—Arrangement: Alternate, simple. Length: About 13.1 cm. Width: About 4 cm. Shape: Narrowly ovate. Apex: Narrowly acute. Base: Attenuate. Margin: Entire, occasionally shallowly dentate. Texture and luster, upper and lower surfaces: Moderately pubescent, strigose; slightly glossy. Venation pattern: Pinnate. Color: Developing leaves, upper surface: Close to 144A. Developing leaves, lower surface: Close to 146B. Fully expanded leaves, upper surface: Darker than between NN137A and 147A; venation, close to 144B. Fully expanded leaves, lower surface: Close to 137B; venation, close to 144B. Petioles, cauline leaves: Length: About 1.3 cm. Width: About 1.5 mm. Height: About 1.5 mm. Strength: Strong, flexible. Texture and luster, upper and lower surfaces: Sparsely pubescent; glossy. Color, upper and lower surfaces: Close to 144B.

Inflorescence description:

*Appearance*.—Large single-type inflorescences with ray and disc florets arranged on a capitulum; inflorescences positioned upright above the foliar plane on strong peduncles.

*Flowering habit*.—Freely flowering habit with about 21 inflorescences developing per plant during the flowering season.

*Fragrance*.—None detected.

*Time to flower*.—Plants begin flowering about 100 days after planting rooted young plants in an outdoor nursery or garden; in the garden, plants flower continuously during the summer, June through August, in The Netherlands.

*Inflorescence longevity*.—Inflorescences maintain good substance for about two weeks on the plant; inflorescences not persistent.

*Inflorescence buds*.—Height: About 2.8 cm. Diameter: About 4.6 cm. Shape: Flattened globular. Texture and luster: Smooth, glabrous; matte. Color: Involucral bracts, close to 144A; developing ray florets, close to 151C.

*Inflorescence size*.—Diameter: About 8.1 cm. Depth (height): About 4.9 cm. Disc diameter: About 3.5 cm.

*Receptacles*.—Height: About 9 mm. Diameter: About 1.1 cm. Color: Close to NN155B.

*Ray florets*.—Quantity and arrangement: About 18 arranged in a single whorl. Length: About 4.8 cm. Width: About 1.1 cm. Shape: Oblanceolate; recurved, not twisting. Apex: Emarginate; shallowly indented. Base: Cuneate. Margin: Entire. Texture and luster, upper surface: Smooth, glabrous, moderately velvety; matte. Texture and luster, lower surface: Smooth, glabrous, slightly velvety; slightly glossy. Aspect: Moderately drooping, about 40° below horizontal. Color: When opening, upper surface: Close to 23A. When opening, lower surface: Close to 11B; towards the margins, close to 13B. Fully opened, upper surface: Close to 14A to 14B; venation, close to 14A to 14B; color does not fade with development. Fully opened, lower surface: Close to 154B to 154C; venation, close to 154B to 154C; color does not fade with development.

*Disc florets*.—Quantity and arrangement: About 300 per inflorescence, arranged spirally at the center of the receptacle. Length: About 1.1 cm. Diameter: About 3.5 mm. Shape: Tubular; proximally, 17.5% free, not fused. Apex: Acute. Base: Fused. Margin: Entire. Aspect: Mostly upright. Texture and luster, inner and outer surfaces: Smooth, glabrous; glossy. Color, when opening, inner and outer surfaces: Apex: Close to 151C. Mid-section and base: Close to 143C. Color, fully opened, inner and outer surfaces: Apex: Close to 151C. Mid-section and base: Close to 143C.

*Receptacle spines*.—Quantity: One per disc floret. Length: About 1.1 cm. Diameter: About 1.5 mm. Shape: Acicular. Apex: Narrowly acute. Base: Cuneate. Texture and luster: Smooth, glabrous; glossy. Color: Apex: Close to 13A. Mid-section: Close to 143C. Base: Close to 145D.

*Involucral bracts*.—Quantity per inflorescence: About 60 arranged in about three whorls. Length: About 9 mm. Width: About 3.5 mm. Shape: Narrowly ovate. Apex: Acute. Base: Cuneate. Margin: Entire; moderately pubescent. Texture and luster, upper and lower surfaces: Smooth, glabrous; slightly glossy. Color, upper surface: Close to 137B. Color, lower surface: Close to 143A.

*Peduncles*.—Length, terminal peduncle: About 16.6 cm. Diameter, terminal peduncle: About 5 mm. Strength: Strong. Aspect, terminal peduncle: Upright. Texture and luster: Moderately pubescent; moderately glossy. Color: Close to 146B with random spots, close to 144C.

*Reproductive organs*.—Androecium (present only on disc florets): Quantity per floret: Five. Filament length: About 3 mm. Filament color: Close to 154C. Anther length: About 3 mm. Anther width: About 0.5 mm. Anther shape: Narrowly oblong. Anther color: Close to 203C. Pollen amount: Moderate. Pollen color: Close to 15A. Gynoecium (present only on disc florets): Quantity per floret: One. Pistil length: About 7 mm. Style length: About 5.5 mm. Style color: Close to 151B. Stigma diameter: About 3.5 mm. Stigma shape: Decurrent, cleft. Stigma color: Close to 151B. Ovary color: Close to 145D. Seeds and fruits: Seed and fruit development have not been observed on plants of the new *Echinacea* to date.

Disease & pest resistance: Plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be suitable for USDA Hardiness Zones 3 to 10.

It is claimed:

1. A new and distinct *Echinacea* plant named 'Sunny292' as illustrated and described.

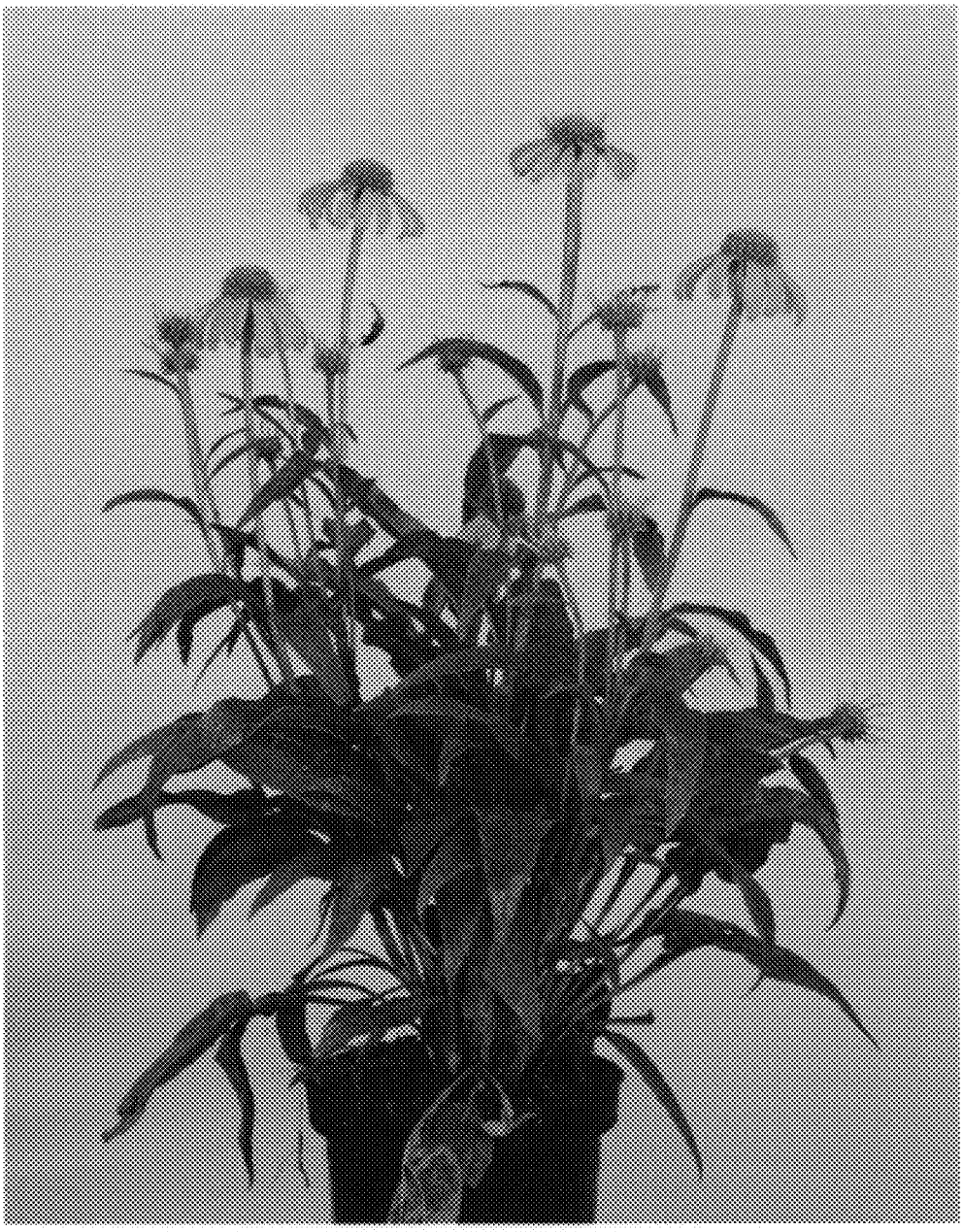

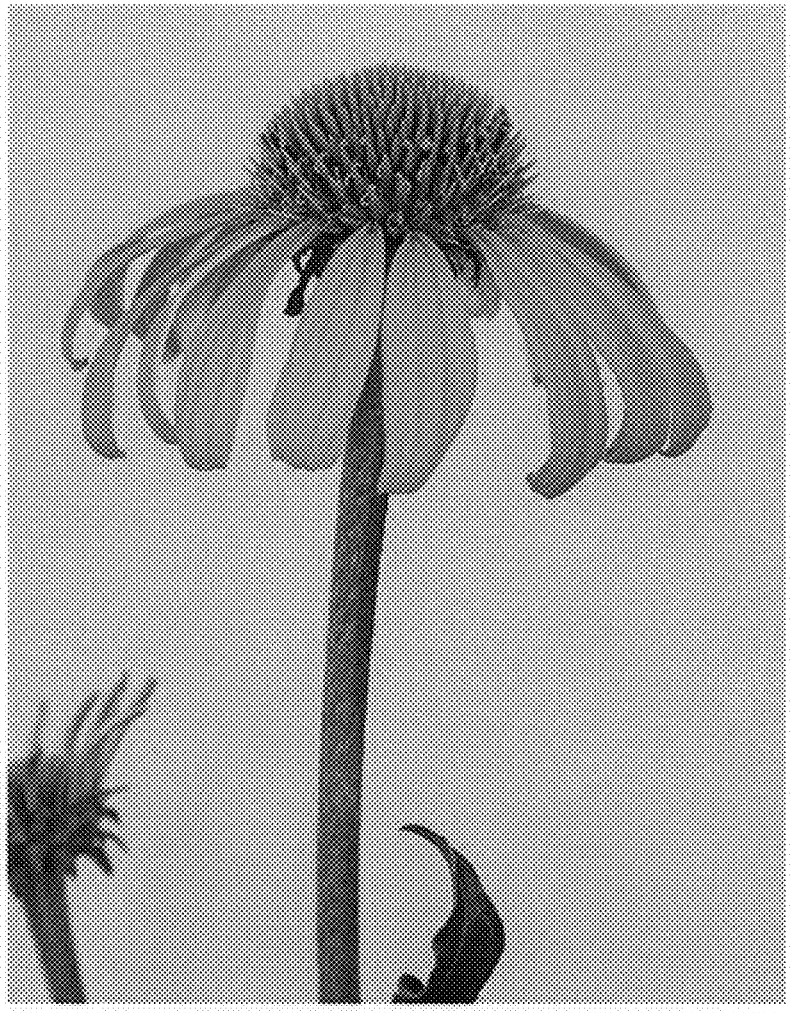
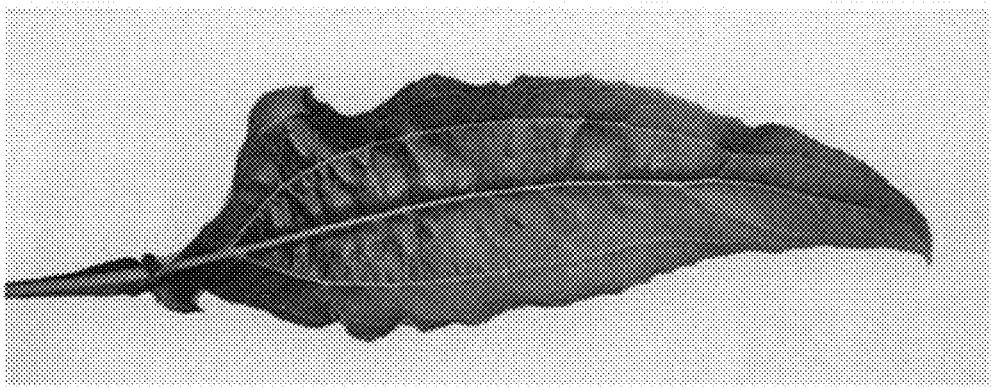

* * * * *